(12) United States Patent
Schmid

(10) Patent No.: US 9,139,764 B2
(45) Date of Patent: Sep. 22, 2015

(54) ORGANIC RADIATION-EMITTING COMPONENT

(75) Inventor: Günter Schmid, Hemhofen (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 771 days.

(21) Appl. No.: 12/680,618

(22) PCT Filed: Sep. 26, 2008

(86) PCT No.: PCT/DE2008/001588
§ 371 (c)(1),
(2), (4) Date: Sep. 7, 2010

(87) PCT Pub. No.: WO2009/039845
PCT Pub. Date: Apr. 2, 2009

(65) Prior Publication Data
US 2010/0320449 A1   Dec. 23, 2010

(30) Foreign Application Priority Data

| Sep. 28, 2007 | (DE) | ................. 10 2007 046 445 |
| Jan. 15, 2008 | (DE) | ................. 10 2008 004 471 |
| Jan. 25, 2008 | (DE) | ................. 10 2008 006 113 |
| Mar. 27, 2008 | (DE) | ................. 10 2008 015 940 |
| May 20, 2008 | (WO) | ................. PCT/DE2008/000868 |

(51) Int. Cl.

| H01L 51/54 | (2006.01) |
| C09K 11/06 | (2006.01) |
| C07D 487/04 | (2006.01) |
| H01L 51/00 | (2006.01) |
| H01L 51/50 | (2006.01) |

(52) U.S. Cl.
CPC .............. *C09K 11/06* (2013.01); *C07D 487/04* (2013.01); *H01L 51/009* (2013.01); *C09K 2211/1007* (2013.01); *C09K 2211/1014* (2013.01); *C09K 2211/1029* (2013.01); *C09K 2211/1044* (2013.01); *C09K 2211/185* (2013.01); *H01L 51/0087* (2013.01); *H01L 51/5016* (2013.01)

(58) Field of Classification Search
CPC ... H01L 51/0087; H01L 51/009; H01L 51/50; H01L 51/5016; C09K 11/06; C09K 2211/1044; C09K 2211/185
See application file for complete search history.

(56) References Cited

U.S. PATENT DOCUMENTS

| 4,797,487 A | 1/1989 | A'Court |
| 6,407,242 B1 | 6/2002 | Okuma et al. |
| 6,420,057 B1 * | 7/2002 | Ueda et al. .................. 428/690 |
| 6,830,828 B2 | 12/2004 | Thompson et al. |
| 6,902,830 B2 | 6/2005 | Thompson et al. |
| 7,001,536 B2 | 2/2006 | Thompson et al. |
| 7,063,901 B2 | 6/2006 | Igarashi et al. |
| 2004/0065544 A1 | 4/2004 | Igarashi et al. |
| 2006/0099451 A1 | 5/2006 | Igarashi |
| 2006/0154106 A1 | 7/2006 | Walters et al. |
| 2006/0222887 A1 | 10/2006 | Okada |
| 2006/0240282 A1 | 10/2006 | Lin et al. |
| 2006/0258043 A1 | 11/2006 | Bold et al. |
| 2007/0048546 A1 | 3/2007 | Ren |
| 2007/0111025 A1 | 5/2007 | Lennartz et al. |
| 2008/0038586 A1 | 2/2008 | Nishizeki et al. |
| 2008/0227979 A1 | 9/2008 | Saalbeck et al. |
| 2009/0212280 A1 | 8/2009 | Werner et al. |

FOREIGN PATENT DOCUMENTS

| CA | 2 549 309 | 9/2005 |
| DE | 10 2004 010 954 | 10/2005 |
| DE | 10 2006 048 592 | 4/2008 |
| DE | 10 2007 012 7 | 6/2008 |
| EP | 1 692 244 | 12/2004 |
| EP | 1 786 242 | 7/2005 |
| JP | 10-226691 | 8/1998 |
| JP | 11-116569 | 4/1999 |
| JP | 11-158185 | 6/1999 |
| JP | 2000-008033 | 1/2000 |
| JP | 2000-229966 | 8/2000 |
| JP | 2001-196637 | 7/2001 |
| JP | 2004-127598 | 4/2004 |
| JP | 2005-298483 | 10/2005 |
| JP | 2007-084635 | 4/2007 |
| JP | 2007-329249 | 12/2007 |
| JP | 2009-521110 | 5/2009 |
| WO | WO 2005/019373 | 3/2005 |
| WO | WO 2005/086251 | 9/2005 |
| WO | WO 2005/097942 | 10/2005 |
| WO | WO 2005/097943 | 10/2005 |

(Continued)

OTHER PUBLICATIONS

Clerac et al. "Completion of the series of M2(hpp)4Cl2 Compounds from W to Pt: The W, Os, and Pt Compounds." Inorg. Chem. 2000. col. 39, pp. 2581-2584.*

Mohamed et al. "Dinuclear and tetranuclear gold-nitrogen complexes. Solvent influences on oxidation and nuclearity of gold guanidinate derivatives." Inorg. Chem. 2007. vol. 46, pp. 11165-11172.*

Trifonov et al. "Postmetallocene lanthanide-hydrido chemistry: A new family of complexes [{Ln{(Me3Si)2NC(NiPr)2}2(µ-H)}2] (Ln=Y,Nd,Sm,Gd,Yb) supported by guanidinate ligands-synthesis, structure, and catalytic activity on olefin polymerization." Chem. Eur. J. 2006, vol. 12, pp. 5320-5327.*

(Continued)

*Primary Examiner* — Michael H Wilson
(74) *Attorney, Agent, or Firm* — Cozen O'Connor

(57) ABSTRACT

An organic radiation-emitting component such as an organic light emitting diode (OLED), having at least two electrode layers and, between them, at least one organic self-emitting layer with a phosphorescence triplet emitter comprising as well as one phosphorescent metal complex. The radiation-emitting layer contains, embedded in a matrix, a metal complex, preferably a transition metal complex, with at least one substituted or unsubstituted guanidinate ligand.

7 Claims, 2 Drawing Sheets

(56) References Cited

FOREIGN PATENT DOCUMENTS

| WO | WO 2006/008976 | 1/2006 |
|----|----------------|--------|
| WO | WO 2006/013738 | 2/2006 |
| WO | WO 2006/098120 | 9/2006 |
| WO | WO 2007/071450 | 6/2007 |

OTHER PUBLICATIONS

F.A. Cotton et al., "The Extraordinary Ability of Guanidinate Derivatives to Stabilize Higher Oxidation Numbers in Dimetal Units by Modification of Redox Potentials: Structures of $Mo_2^{5+}$ and $Mo_2^{6+}$ Compounds", Journal of American Chemical Society, vol. 124, pp. 9249-9256, Jul. 10, 2002.

F.A. Cotton et al., "Strong reducing agents containing dimolybdenum $Mo_2^{4+}$ units and their oxidized cations with $Mo_2^{5+/6+}$ cores stabilized by bycyclic guanidinate anions with seven-membered ring", The Royal Society of Chemistry, Dalton Trans. pp. 4623-2631, Jul. 25, 2006.

F.A. Cotton et al., "Homologues of the Easily Ionized Compound $Mo_2(hpp)_4$ Containing Smaller Bicyclic Guanidinates", American Chemical Society, Inorganic Chemistry, vol. 45, No. 15, pp. 5493-5500, 2006.

F.A. Cotton et al., "Closed-Shell Molecules That Ionize More Readily Than Cesium", www.sciencemag.org, Science vol. 298, pp. 1971-1974, Dec, 6, 2002.

J.F. Berry et al., "A hardwon dirhodium paddlewheel with guanidinate type (hpp) bridging ligands", Dalton Transactions, pp. 3713-3715, XP002512869, Oct. 21, 2005.

Bailey et al. "A New Bridging Ligand for the $[Mo_2]^{4+}$ Dimer: Syntheses and X-ray Crystal Structures of the Redox Pair $[Mo_2\{u-n^2 -(NPh)_2 CNHPh\}_4]^{0/+}$", Inorg. Chem. 1997, vol. 36, pp. 867-871 and correction vol. 36, No. 23, p. 5420, 1997.

Bailey et al. "Spectroscopic and Structural Properties of Binuclear Platinum-Terpyridine Complexes", Inorg. Chem. vol. 32, No. 4, Feb. 17, 1993, pp. 369-370.

Boydston et al., "Synthesis and Study of Bidentate Benzimidazolylidene-Group 10 Metal Complexes and Related Main Chain Organometallic Polymers", Organometallics (2006), Bd. 25, Nr. 26, pp. 6087-6098.

Brooks et al., "Synthesis and Characterization of Phosphorescent Cyclometalated Platinum Complexes" Inorg. Chem., vol. 41, No. 12, 2002, pp. 3055-3066.

Coleman et al., "Silver(I) Complex of a New Imino-N-heterocyclic Carbene and Ligand Transfer to Palladium (II) and Rhodium(I)", Journal of the Chemical Society, Dalton Transactions (2003), pp. 2917-2922.

Cotton et al. "Better Understanding of the Species with the Shortest $Re_2$ 6+ Bonds and Related $Re_2$ 7+ Species with Tetraguanidinate Paddlewheel Structures", Inorg. Chem. vol. 46, No. 5, 2007, pp. 1718-1726.

Cotton et al. "Pramagnetism at Ambient Temperature, Diamagnetism at Low Temperature in a $Ru2^6$ + Core: Structural Evidence for Zero-Field Splitting", Inorg. Chem. vol. 43, 2004, pp. 8373-8378.

Cotton, et al. "Multiple Bonds Between Atoms", 1964, pp. 1-21.

Ketz et al., "Structure and Reactivity of an Allylpalladium N-Heterocyclic Carbene Enolate Complex", Organometallics, Bd. 23, Nr. 12 (2004), pp. 2835-2837.

Ketz et al., "Synthesis, Structure, and Olefin Polymerization with Nickel(II) N-Heterocyclic Carbene Enolates", Chemical Communications, Bd. 45 (2005), pp. 5693-5695.

Moser et al., "1, 8-Bis(Imidazolin-2-Yliden-l-y1)Carbazolide (bimca): A New CNC Pincer-Type Ligand with Strong Electron-Donating Properties. Facile Oxidative Addition of Methyl Iodide to Rh(bimca)(CO)", Organometallics (2007), Bd. 26, Nr. 4, pp. 1024-1030.

Ratilla et al. "Terminal and New Bridging Coordination of Methylguanidine, Arginine, and Canavanine to Platinum (II). The Frist Crystallographic Study of Bonding between a Transition Metal and Guanidine Ligand", Inorg. Chem. vol. 29, No. 5, 1990, pp. 918-926.

Ren et al. "A New Class of o-hydroxyaryl-substituted N-heterocyclic carbine ligands and their complexes with palladium", Journal of Organometallic Chemistry, Bd. 692, Nr. 10 (2007), pp. 2092-2098.

\* cited by examiner

ORGANIC RADIATION-EMITTING COMPONENT

RELATED APPLICATIONS

This is a U.S. national stage of application No. PCT/DE2008/001588, filed on Sep. 26, 2008.

This application claims the priority of German Patent Applications 10 2007 046 445.4 filed Sep. 28, 2007, 10 2008 015 940.9 filed Mar. 27, 2008, 10 2008 006 113.1 filed Jan. 25, 2008 and 10 2008 004 471.7 filed Jan. 15, 2008 and PCT/DE2008/000868 filed May 20, 2008, the disclosure content of all of which is hereby incorporated by reference.

This invention pertains to an organic radiation-emitting component such as an organic light emitting diode (OLED), which comprises at least two electrode layers and between them, at least one organic radiation-emitting layer with a triplet emitter, as well as a phosphorescent metal complex suitable therefor.

BACKGROUND OF THE INVENTION

The prior art makes available a number of OLEDs emitting red and/or green light. OLEDs that radiate deep blue, light blue and/or blue-green and having acceptable, i.e. economically more attractive, life spans are less common.

Cotton et al. showed that the hpp ligand (anion of 1,3,4,6,7,8-hexahydro-2H-pyrimido[1,2-a]primidine=Hhpp) has the extraordinary ability of stabilizing complexes in high oxidation states because of its enormous basicity (F. A. Cotton, L. M. Daniels, C. A. Murillo, D. J. Timmons, C. C. Wilkinson, J. Am. Chem. Soc. 2002, 124, 9249-9256, and Tab. 3 from F. A. Cotton, N. E. Gruhn, J. Gu, P. Huang, D. L. Lichtenberger, C. A. Murillo, L. O. van Dorn, C. C. Wilkinson; "Closed-Shell Molecules That Ionize More Readily Than Cesium," Science Vol 298 (2002) 1971.).

SUMMARY OF THE INVENTION

It is an object of this invention is to make available an improved OLED.

One aspect of the invention is directed to a radiation-emitting organic component having a substrate, at least one lower electrode layer, at least one organic radiation-emitting layer, and, in addition, at least one upper electrode layer, wherein at least one radiation-emitting metal complex that has at least one ligand that is coordinated at the central atom via a guanidine anion group is contained in a matrix in the emitting layer. Subsequently, such a ligand, which is a guanidine anion or contains an anionic guanidine group, is also called guanidinate ligand.

Advantageously, the metal complex embedded in the matrix in the emission layer contains at least one anionic ligand that contains the structural unit of an anion derived from guanidine, thus the guanidine anion group:

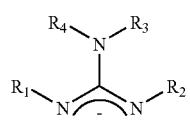

This guanidinate ligand can be substituted or unsubstituted.

Other metal complexes with low ionization enthalpies are also known from the above cited Science-article of Cotton et al. These metal complexes up to now were used for n-doping of organic semiconductor materials. Selected examples of such metal complexes to which the so-called "hpp" ligand, a "paddlewheel" ligand, is bonded are given in the following table, which is taken from the said article of Cotton et al.

TABLE 3

First ionizations of atoms and chemically prepared and isolated molecules below 5 eV. Transient and low-temperature species detected in molecular beam techniques are discussed in the text. All of the dinuclear molecules have closed-shell singlet $\sigma^2\pi^4\delta^2$ configurations.

| Molecule or atom | Spin state | IE (eV) | Type | Ref. |
|---|---|---|---|---|
| $W_2(hpp)_4$ | | 3.514 | Onset | This work |
| $W_2(hpp)_4$ | | 3.76 | Vertical | This work |
| Cs | Doublet | 3.89 | Atomic | (3, 22, 23) |
| $(\eta^6\text{-}C_6Et_6)(\eta^5\text{-}C_5Me_5)Fe$ | Doublet | 3.95 | Onset | (23) |
| $Mo_2(hpp)_4$ | | 4.01 | Onset | This work |
| Fr | Doublet | 4.07 | Atomic | (22, 23) |
| Rb | Doublet | 4.18 | Atomic | (3, 22, 23) |
| $(\eta^6\text{-}C_6Et_6)(\eta^5\text{-}C_5Me_5)Fe$ | Doublet | 4.21 | Vertical | (23) |
| $Mo_2(hpp)_4$ | | 4.33 | Vertical | This work |
| K | Doublet | 4.34 | Atomic | (3, 22, 23) |
| $Cp(\eta^6\text{-}C_6Et_6)Fe$ | Doublet | 4.54 | Vertical | (24) |
| $Cp(\eta^6\text{-}C_6Me_6)Fe$ | Doublet | 4.68 | Vertical | (24) |
| $(\eta^5\text{-}C_5Me_5)_2Co$ | Doublet | 4.71 | Vertical | (25) |
| $Cp(\eta^6\text{-}C_6H_3(CMe_3)_3)Fe$ | Doublet | 4.74 | Vertical | (24) |
| $Cr_2(hpp)_4$ | | 4.76 | Onset | This work |
| $(\eta^5\text{-}C_9Me_7)_2Co$ | Doublet | 4.89 | Vertical | (26) |
| $(\eta^5\text{-}C_5Me_5)_2Cr$ | Triplet | 4.93 | Vertical | (25) |
| $Cr_2(hpp)_4$ | | 5.00 | Vertical | This work |

Surprisingly, it turned out that metal complexes with the "hpp" ligand disclosed there and also, generally, metal complexes with guanidinate ligands lead to efficient short-wave emission in emitter systems or emitter layers for organic light emitting diodes and in doing so also show sufficient stability. The emitters are suitable, for example, for emission of red radiation, orange radiation, yellow radiation, green radiation, blue radiation and violet radiation. One may also mention in particular emitters that emit deep blue (less than about 450 nm), light blue (about 450-500 nm) and/or blue-green (above about 500 nm). One or more (like or different) other ligands (subsequently called coligands) can also be contained in the metal complexes, in addition to the said guanidinate ligands.

Advantageously, the metal complex comprises a transition metal atom or a lanthanoid as the central atom, in particular a transition metal of groups 7, 8, 9, 10 or 11 of the periodic system, preferably Ir, Pt, Au, Re, Rh, Ru, Os, Pd, Ag, Zn; iridium, platinum and gold are especially preferred. Thereby, also more than one substituted or unsubstituted guanidinate ligand can be bound.

In the following, the possible binding capacities in accordance with an embodiment of the invention of the guanidinate ligands to the metal centers are shown with an hpp ligand as an example. The ligand can be coordinated only to a metal center or can be a bridging ligand. Mixed variations, where an hpp ligand is bonded bidentately to a first metal atom, while another acts as a bridging ligand to the first metal atom and a second metal atom, also fall within the scope of the invention.

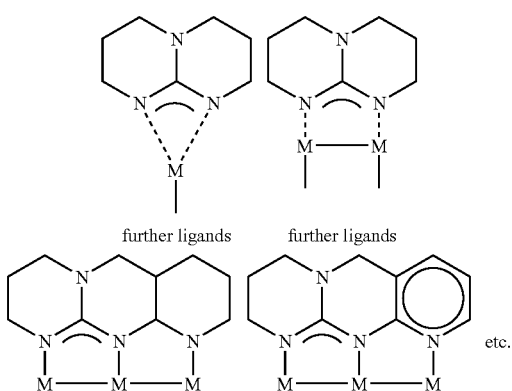

further ligands   further ligands etc.

The coordination sphere of the metal atom is optionally completed by other coligands of any kind, in particular also ligands derived from a guanidine backbone.

In accordance with an embodiment of the invention, not only complexes with the hpp ligand itself proved to be advantageous in the emission layers of radiation-emitting components, but also in particular ligands with a guanidine backbone modified in various ways.

Up to now guanidinate ligands were not used for emitter systems, since there was a scientific prejudice that incompletely conjugated ligands like those with the guanidine group would not be suitable for emitter systems. In this respect, a completely conjugated ligand is understood to be a ligand that contains at least one aromatic compound and/or a plurality of conjugated double bonds.

According to an embodiment of the invention, it was established, in contrast, that guanidinate ligands can be employed for stabilization in organometal phosphorescent emitters, even though a completely conjugated system is not present in these emitters. Therefore, the emission wavelength of the guanidinate complexes in accordance with the invention can also be determined by the coligands. In addition, it was established that the guanidinate ligand stabilizes the emitting complex against electrons. The guanidinate ligands can in this case contain additional substitutes that continue the coordination to other metal atoms. In this case polynuclear complexes arise.

Thus, the metal complex embedded in the matrix of the emission layer contains at least one anionic ligand with the general structural formula:

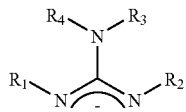

By varying residues $R_1$, $R_2$, $R_3$ and $R_4$, various types of ligands that are suitable for the emitter systems in a component in accordance with the invention can be produced. $R_1$, $R_2$, $R_3$ and $R_4$ can independently be H, unbranched (for example, methyl, ethyl), branched, condensed (for example, decahydronaphthyl) and cyclic (for example, cyclohexyl) alkyl residues, aromatic compounds, condensed aromatic compounds, heterocycles and condensed heterocycles as well as optionally completely or partially substituted alkyl residues, aromatic compounds, condensed aromatic compounds, heterocycles and condensed heterocycles.

In addition, groups $R_1$ and $R_4$ and/or groups $R_2$ and $R_3$ (and optionally also groups $R_3$ and $R_4$) can be bonded to each other and in particular represent an alkylene bridge, so that a ring, which in particular can be a 5- or 6-member ring, is formed. The alkyl residues and alkylene residues can contain ether groups (ethoxy, methoxy, propoxy, etc.), ester, amide, carbonate groups, etc. As mentioned, $R_1$, $R_2$, $R_3$ and $R_4$ are not limited to saturated systems, but rather can also involve the following residues or consist thereof: substituted or unsubstituted aromatic compounds and heterocycles. One may mention in particular as aromatic compounds: phenyl, diphenyl, naphthyl, phenanthryl, etc., or benzyl, etc. A compilation of possible heterocycles is shown below:

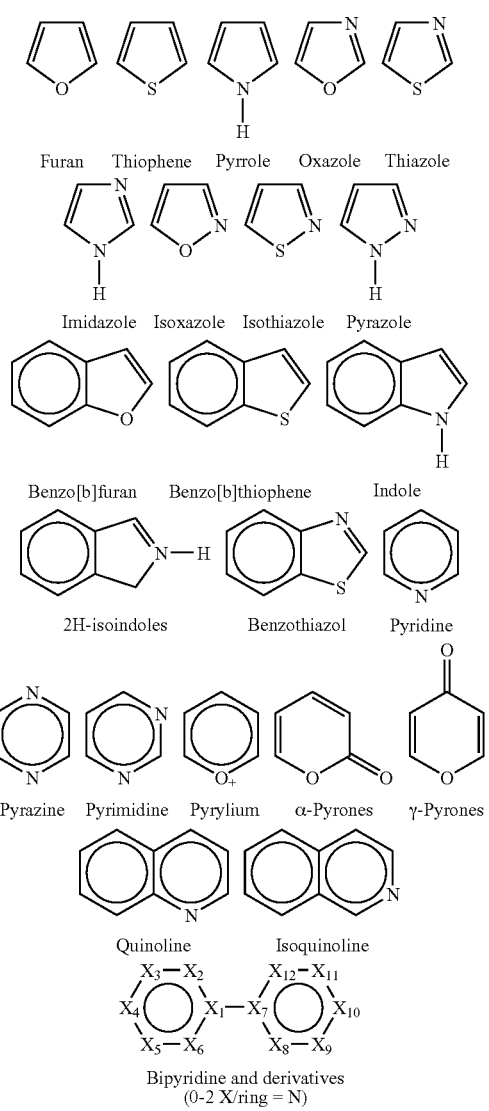

This is only a selection of substituted or unsubstituted heterocycles that are possibilities as residues $R_1$, $R_2$, $R_3$ and $R_4$ or as a component of these residues. For the sake of simplicity only the basic unit is shown. The binding of the ligands can take place at any site of the parent substance or at a linker. In addition, these residues themselves can additionally be substituted, for example by electron-withdrawing or electron-donating groups.

Possible coligands are all ligands and ligand systems that up to now were described in complexes used for emitters in organic self-emitting components, for example in OLEDs (organic light emitting diodes), or described as suitable for this use. Basically essentially monodentate, bidentate or polydentate coligands coordinated at the central atom via a C, N, P, As, Sb, O, S and/or Se atom are suitable. Some known examples of coligands are found, for example, in WO2005097942A1, WO2006013738A1, WO2006098120A1, WO2006008976A1, WO2005097943A1 or U.S. Pat. Nos. 6,902,830, 7,001,536, 6,830,828. Therefore, in accordance with the invention a large number of at least bidentate ligands that are coordinated to the metal atom via a C atom and an N atom or via two N atoms (example: 2-phenylpyridine or 2-phenylimidazole) are suitable for use as coligands in emitters for organic light emitting diodes.

Also suitable as coligands are ligands that are obtained via fluorination of the phenylpyridine ligands in bis(2,4-difluorophenyl-2-pyridyl)iridium(III) picolinate (FIrPic) or bis(2,4-difluorophenylpyridinato)tetrakis(1-pyrazolyl)borate iridium(III) (FIr6). The fluorination shifts the emission toward shorter wavelengths. In addition, carbene ligands are suitable (WO200519373 or EP1692244B1); thereby electronic structures that generate a deep blue emission are produced by increasing the electron density.

The content of the publications mentioned in reference to the coligands, especially concerning structure and synthesis of the coligands, is herewith intended to be a part of the disclosure of this description by reference. All compounds in the said patents are included in this application, provided they satisfy the described conditions through the claimed modification.

In contrast to metal complexes that exclusively contain coligands, the complexes in accordance with the invention with ligands that are coordinated to the central atom via a guanidine anion group contained therein exhibit improved stability and easier accessibility.

Preferably, at least one central atom is stabilized in particular in oxidation state Ir(III), Pt(II) and/or Au(I) in homo- or heteroleptic organometal complexes by the ligands that are coordinated to the central atom via a guanidine anion group contained therein, where the emission spectrum of the complex, insofar as the said coligands are contained, is shifted to shorter emission wavelengths and/or the stability to electrons in the end OLED component is increased.

Some exemplary suitable guanidinate ligands are indicated below for illustration:

Especially preferred is the hpp anion itself (below designated with 5a). The length of the two bridges that bond the two nitrogen atoms can independently be varied (below designated with 5b). Here n or m are integers that independently can be chosen between 1 and 10, where n and/or m is preferably 2, 3, or 4. The structure below designated with shows as an example the bridged guanidine backbone with n and m=3. The substituents $R_1$-$R_{12}$ can be the same or different and have the same meaning as substituents $R_1$-$R_4$ that were defined above for the general structure of the guanidinate ligand. However, in contrast, in structure 5c two substituents of adjacent carbon atoms can be bonded together, and in particular are alkylene bridges, so that one, two or more rings are formed, which independently can be in particular 5- or 6-member rings.

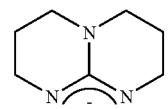

5a

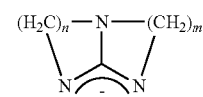

5b

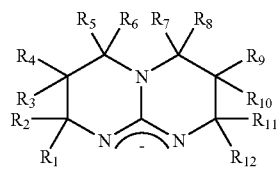

5c

Additionally suitable are compounds of the following structures 6a and 6b; they show a derivative with condensed aromatic ring systems. Especially preferred here is n=0, 1, 2 and m—0, 1, 2. Substituents $R_1$-$R_4$ in structure 6b can be the same or different and have the same meaning as substituents $R_1$-$R_4$ defined above for the general structure of the guanidinate ligand.

from what was defined there, in structure 6b the substituents $R_1$ or $R_2$ can be bonded to the substituents $R_3$ or $R_4$ and in particular are an alkylene bridge, so that a ring is formed that in particular can be a 5- or 6-member ring. The substituents $R_5$ and $R_6$ in structure 6a and 6b stand for a complete substitution pattern that also can be formed from several individual substituents, which each can have the meaning given above for residues $R_1$-$R_4$.

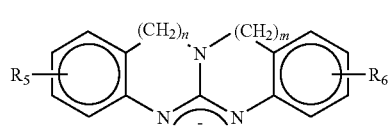

6a

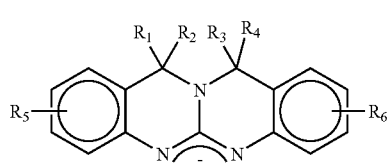

6b

Further suitable are compounds of the following structures 7a-7c. They show different ligands with a central guanidine nucleus and aromatic substituents. These can be individual (7a), bridging—where both bridges between different aromatic substituents (7b) and bridges between two substituents $R_x$ bonded to the same aromatic substituent can be present—or condensed (7c). $R_x$ (x=1-4) can be the same or different and are in each case one or more substituents bonded to a ring that are defined as above for the general structure of the guanidinate ligand.

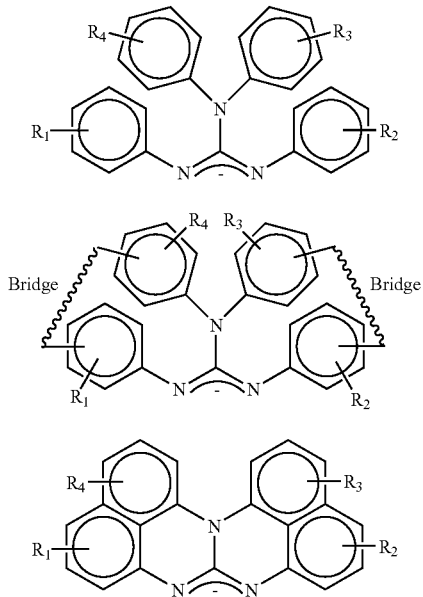

Also suitable are compounds of the following structures 8a-8d and 9a-9h. Structures 8a-8d are guanidine derivatives with saturated ring systems or substituents. $R_x$ (x=1-4) can be the same or different and in each case are one or more substituents bonded to a ring that are defined as above for the general structure of the guanidinate ligand.

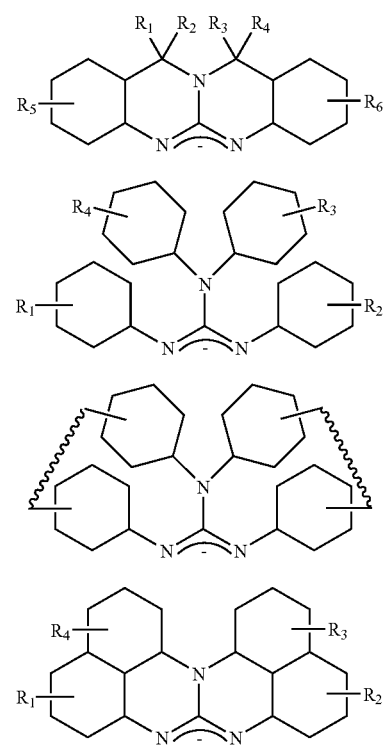

Structures 9a-9h are mixed or more highly condensed variations of structures 7a-7d and 8a-d.

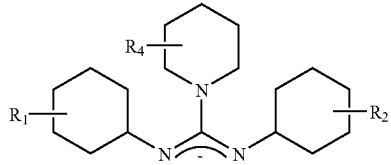
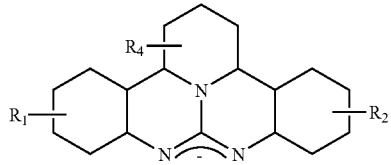
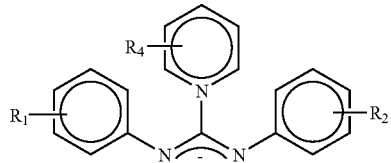
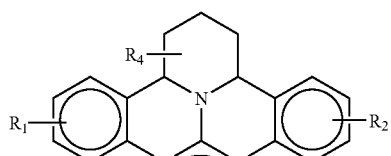

In an embodiment of the invention also Guanidine derivatives that contain additional heterocyclic substituents (aromatic or aliphatic) are suitable. Some structural formulas that show guanidine derivatives with fused hexacyclic rings are shown below. In the case of aromatic rings $X_1$-$X_{10}$ can independently be C—H or C—R or N. In the case of aliphatic rings $X_1$-$X_{10}$ can independently be $CH_2$, C—HR or C—$R_1R_2$ or N or NH or NR. The residues R or $R_1$ or $R_2$ can here each be the same or different and represent substituents that are defined as above for the general structure of the guanidinate ligand.

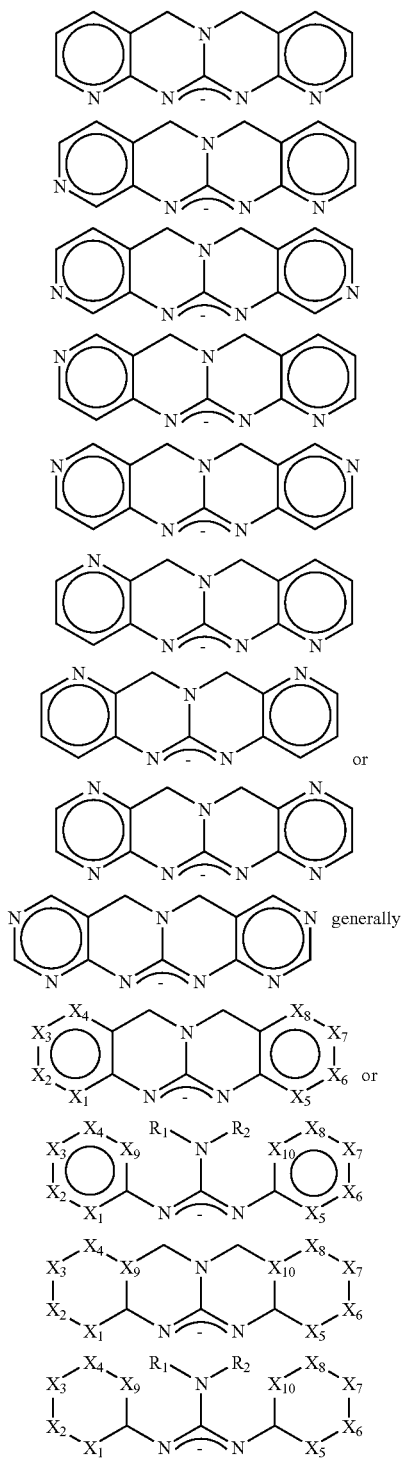

Analogously, representatives of the said guanidine derivatives with fused quinoline and isoquinoline groups are also suitable. Additionally suitable are guanidine derivatives in which the aromatic rings indicated above are also hydrogenated and/or substituted with one or more substituents R (The residues R in this case can be the same or different and are substituents that are defined as above for the general structure of the guanidinate ligand).

Finally, guanidine derivatives of the following structures (with imidazole or benzimidazole substituents) are also suitable. Substituents $R_1$-$R_8$ here can be the same or different and are substituents that are defined as above for the guanidine anion group. However, if at least $R_1$ or $R_2$=H, there is the possibility of obtaining twofold negatively charged ligand systems by an additional deprotonation. Analogously, guanidine derivatives with pyrazole groups are also suitable.

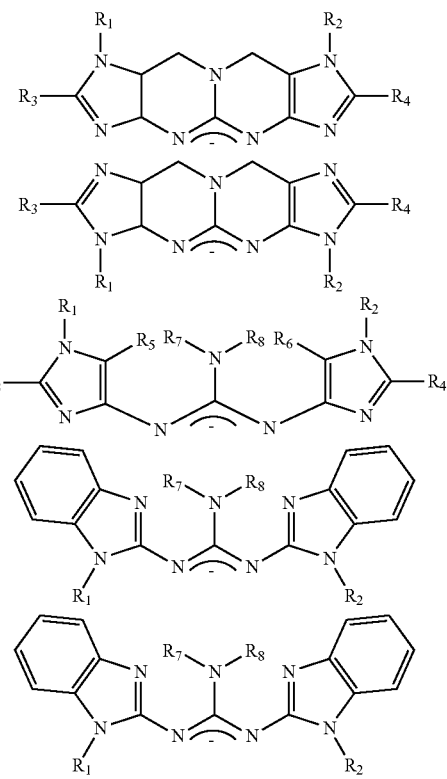

Further, ligands with a guanidine backbone that additionally contain P, S, O, As, Sb, F, or also organometal substituents such as ferrocenyl, phthalocyaninyl (where the central atom can be Zn, Fe, Ni, etc.) are suitable within the scope of the invention.

With the invention one can identify for the first time a structural element that can be employed to increase the stability in organometal phosphorescent emitters, in particular in triplet emitters. The ligands in accordance with an embodiment of the invention involve the anion of a guanidine derivative that can be coordinated to metal atoms in various ways. The anionic ligands are obtained by deprotonation of the corresponding neutral ligand with guanidine unit. The ligand systems can contain additional substituents that advance the coordination to other atoms.

DETAILED DESCRIPTION OF THE DRAWINGS

Figure 1:
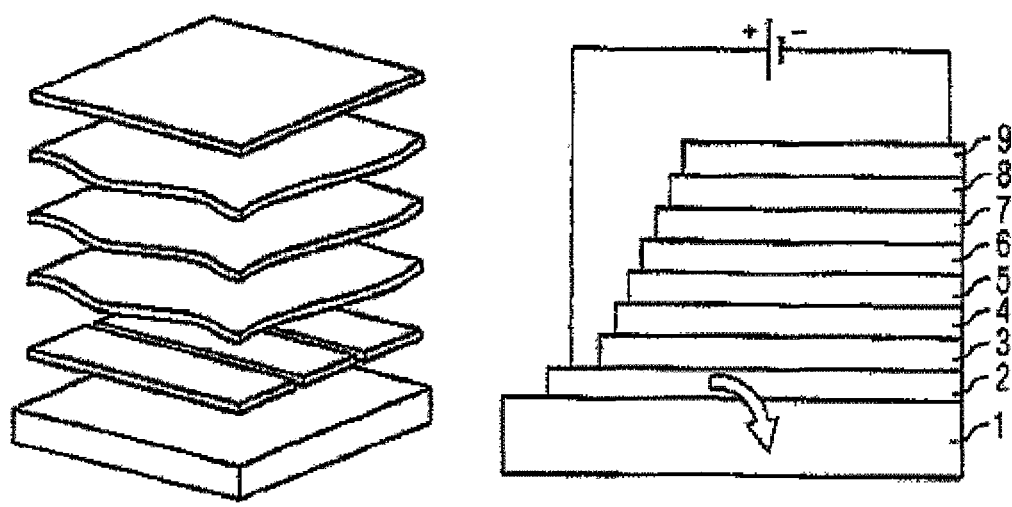
FIG. 1 shows a schematic side view of a radiation-emitting component.

FIG. 1 schematically shows the structure of an organic self-emitting component. Starting from the bottom and going up, the following layer structure is realized:

Substrate 1, which can, for example, be transparent and be made of glass is located at the very bottom. Thereupon, the lower electrode layer 2 is located, which can, for example, be a transparent conducting oxide such as zinc oxide, tin oxide, cadmium oxide, titanium oxide, indium oxide or indium tin oxide (ITO). Upon this electrode layer the hole injection layer 3 is located, upon which in turn the hole transport layer 4 is located upon which the organic active layer, the emission layer 5, is located. Upon the emission layer 5 is the hole blocking layer 6 is located, upon which the electron transport layer 7 and finally the electron injection layer 8 with adjacent upper electrode 9 is located, for example a metal electrode or another transparent electrode, for example made of the transparent conducting oxides mentioned above.

If a voltage is applied between the upper and lower electrodes, current flows through the component, and photons are released in the organic active layer 5, which leave the component in the form of light via the lower electrode 2 and the substrate 1.

In accordance with an embodiment of the invention, metal complexes that have an ionization potential less than or equal 5 eV are provided in a matrix in the emission layer 5. In particular, the metal complexes in accordance with the invention that have at least one ligand that coordinates to the central atom via a guanidine anion group are provided.

The production of such a radiation-emitting component can take place, for example, as follows:

First an ITO layer is deposited as anode on a glass plate by HF sputtering. To deposit the additional functional layers this substrate is placed in a vessel; the vessel contains one or more sources in which organic material (to produce the individual functional layers of the radiation-emitting device such as emitter materials or p- or n-dopants) can be evaporated. In addition, one or more sources for delivery of one or more different matrix materials are provided. To form a hole injection layer, deposition is carried out jointly from a source with matrix material and a source with p-dopant onto the glass plate with the anode. The joint deposition of dopant and matrix material for the hole transport layer takes place correspondingly. Subsequently, codeposition of a matrix material and the metal complex in accordance with the invention and optionally another phosphorescent compound takes place, and the emitter layer is obtained. The deposition of other layers like a blocking layer, electron transport layer and electron injection layer takes place analogously. Finally, a 150 nm thick aluminum layer is formed as a reflective electrode.

Below embodiment examples for preparation of transition complex compounds are given.

Guanidine derivatives can be synthesized, for example, by the preparation methods according to Dalton Trans., 2006, 4623-4631, Inorganic Chemistry, 2006, 45, 5493-5500 and Inorg. Chem. 1997, 36, 867, and according to WO 2005/086251 A2, U.S. Pat. No. 4,797,487 and EP 0 198 680 A1. The triamines required for these syntheses can be obtained, for example, according to FI 82445. Reference is hereby made to these preparation methods in their entire contents.

1. General Procedure for Producing Bicyclic Guanidine Derivatives:

100 mmol carbon disulfide are added to a solution of 100 mmol triamine in 150 mL p-xylene. The resulting mixture is then heated at reflux until hydrogen sulfide is no longer formed (about 10 days). The bicyclic guanidine can be purified by crystallization by chilling the xylene solution and usually also by sublimation.

The synthesis is shown below by means of a substituted or unsubstituted N-3-aminopropyl-1,3-propanediamine:

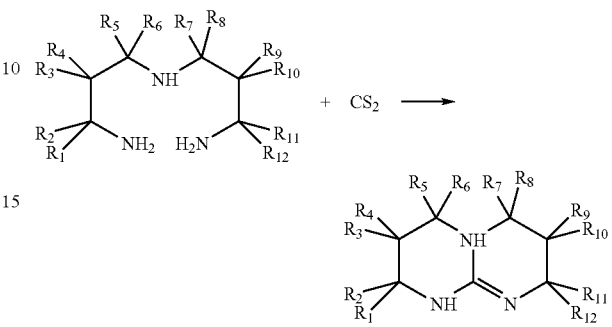

2. General Procedure for Preparation of Monocyclic or Acyclic Guanidine Derivatives:

100 mmol of the thiourea derivative are added to a solution of 100 mmol primary amine in 150 mL p-xylene. The resulting mixture is then heated at reflux until hydrogen sulfide is no longer formed (about 10 days). The resulting guanidine derivative can be purified by crystallization by cooling the xylene solution and usually also by sublimation:

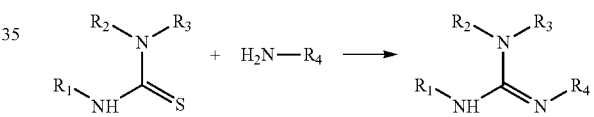

3. General Procedure for Preparation of Complexes with Guanidinate Ligands:

1 mmol of a metal salt of the formula $L^1_k L^2_m MX_n$ or the formula $[L^1_k L^2_{m-1} MX_n]_2$ is suspended in 20 mL dichloromethane or in 20 mL tetrahydrofuran and chilled to $-70°$ C. Then n*1 mmol sodium methylate (or alternatively butyllithium) and n*1 mmol guanidine derivative are each suspended in 40 mL dichloromethane (herein corresponds to the number of guanidinate ligands to be coordinated), and this is likewise chilled to $-70°$ C. This suspension is slowly added dropwise to a suspension of the metal salt. The reaction mixture is stirred for 48 h at room temperature. Then it is filtered through a frit and washed with dichloromethane. The filtrate is concentrated and vacuum dried. Optionally, the resulting guanidine complex can be purified by washing it with pentane.

In the above formula of the metal complex $L^1$ corresponds to any ligand; k corresponds to the number of $L^1$ ligands coordinated per metal and can also be 0; $L^2$ corresponds to any neutral ligand, which is eliminated in the reaction with the guanidinate ligand (for example, a $C_2H_4$ ligand); m corresponds to the number of $L^2$ ligands coordinated per metal and is >0, for monodentate neutral ligands (for example, $C_2H_4$) m-1=n; x is a halogen ligand or another ligand with a single negative charge (for example, a carboxylate ligand like acetate); n corresponds to the number of guanidinate ligands to be coordinated or the number of ligands X.

4. Synthesis of di(μ-chloro)bis[(phenylpyridino)platinum(II)]=Compound 1

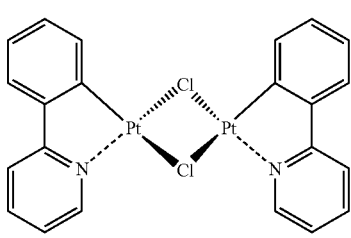

Compound 1

12 mmol (4.98 g) potassium tetrachloroplatinate are dissolved in 24 mL hot degassed water and again chilled with vigorous stirring. The potassium tetrachloroplatinate precipitates as a fine suspension. A solution of 12 mol (1.86 g) phenylpyridine in 72 mL ethoxyethanol is added dropwise to this suspension. The suspension is heated to 70° C., whereupon a dark green precipitate increasingly forms. 30 mL water are added as a lower layer to the suspension and stirred for about 2 h, in order to precipitate the raw product. The raw product is vacuum filtered out and washed several times with a water/alcohol mixture (10:1). At this point the product becomes air-stable. Then it is vacuum dried for about 20 h. Various batches show in the solid substance a yellow to green coloration, in each case according to the amount of contaminants. The raw product, however, can be used for the following experiments without further purification.

Yield: 3.56 g (77.2%).

5. Synthesis of di(μ-chloro)bis[(2,4-difluorophenylpyridino)platinum(II)]=Compound 2

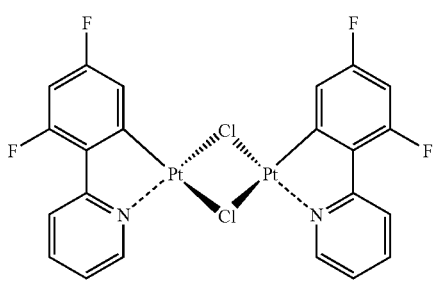

Compound 2

7.23 mmol (3 g) potassium tetrachloroplatinate are dissolved in 14 mL hot degassed water and chilled to 30° C. under vigorous stirring. The potassium tetrachloroplatinate precipitates as a fine suspension. A solution of 7.23 mmol (1.387 g) 2,4-difluorophenylpyridine in 42 mL ethoxyethanol is slowly added dropwise to this suspension. The suspension is heated to 70° C. for about 20 h whereupon a yellow-green precipitate increasingly forms. A bottom layer of 30 mL water is added to the suspension after it has warmed to room temperature, to precipitate the raw product, and the suspension is stirred for about 2 h. The yellow-green raw product is vacuum filtered out and washed several times with water/alcohol mixture (10:1). It is vacuum dried in a desiccator for about 20 h.

Yield: 2.36 g (78%)

6. Synthesis of di(μ-chloro)bis[(dipyridylamino)platinum(II)]=Compound 3

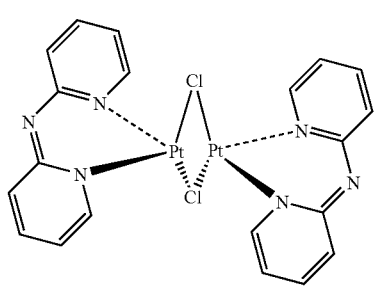

Compound 3

3 mol (1.245 g) potassium tetrachloroplatinate are dissolved in 6 mL hot degassed water and cooled to 30° C. with vigorous stirring. The potassium tetrachloroplatinate precipitates as a fine suspension. A solution of 3 mmol (0.541 g) dipyridylamine in 45 mL ethoxyethanol is slowly added dropwise to this suspension. The suspension is heated for about 20 h to 70° C., and a cream-colored precipitate increasingly forms. A bottom layer of 40 mL water is added to the suspension after cooling it to room temperature to precipitate the product, and the suspension is stirred for about 2 h. The raw product is vacuum filtered out and washed several times with a water/alcohol mixture (10:1). It is vacuum dried in a desiccator for about 20 h.

Yield: 1 g (83%).

7. Synthesis of di(μ-hpp)-bis[(phenylpyridino)platinum(II)]=Compound 4

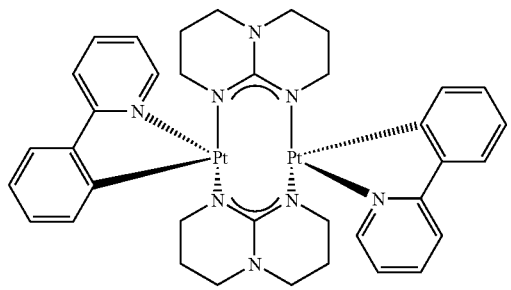

Compound 4

0.39 mmol (0.3 g) di(μ-chloro)bis[(phenylpyridino)platinum(II)] (Compound 1) is suspended in 25 ml, dichloromethane. At the same time 0.78 mmol (108.6 mg) Hhpp and 0.78 mmol (42.13 mg) sodium methylate are suspended in 20 mL dichloromethane. Both suspensions are cooled to −70° C. while stirring, and then the Hhpp suspension is added to the di(μ-chloro)bis[(phenylpyridino)platinum(II)] suspension. The mixture is stirred for about 48 h at room temperature. After 48 h the mixture is filtered through a P4 frit and washed several times with dichloromethane. The solution is concentrated in a vacuum. Then the substance is washed with pentane. The pentane extract, however, shows the same result in the photoluminescence spectrum as the washed product.

Yield: practically quantitative.

Figure 2A:
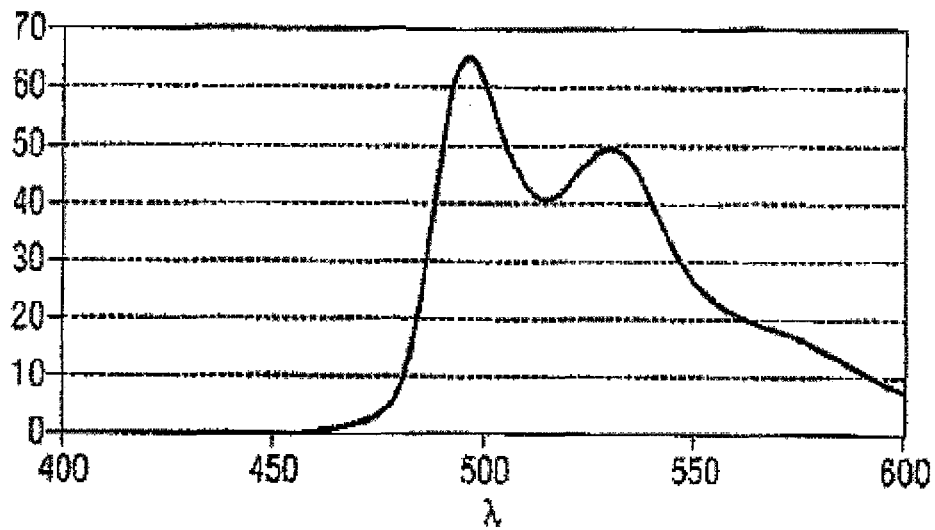
FIGS. 2a-c show photoluminescence spectra for different metal complex compounds.

FIG. 2a shows the photoluminescence spectrum of Compound 4, with emission peaks at 498 nm and 531 nm.

8. Synthesis of di(μ-hpp)bis[(2,4-difluorophenylpyridino)platinum(II)]=Compound 5

Compound 5

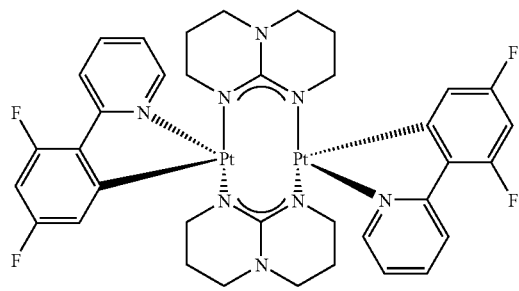

1.19 mmol (1 g) di(μ-chloro)bis[(2,4-difluorophenylpyridino)platinum(II)] (Compound 2) are suspended in 20 mL dichloromethane and chilled to −70° C. A mixture of 2.377 mmol (128.4 mg) sodium methylate and 2.377 mmol (330.9 mg) Hhpp suspended in 40 mL dichloromethane and likewise chilled to −70° C. is added to the above mixture. The greenish reaction mixture is stirred for 48 h at room temperature, and the mixture turns brownish. Then it is filtered through a frit and washed with dichloromethane. The filtrate is concentrated, yielding a brownish-beige product. A fraction dissolved out with ether gives the same PL spectrum as the crude product.

Yield: practically quantitative.

Figure 2B:
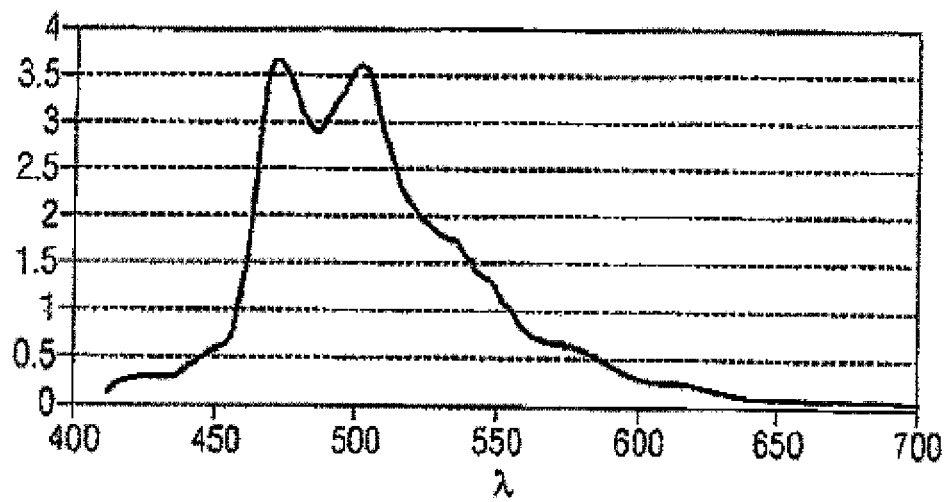

FIG. 2b shows the photoluminescence spectrum of Compound 5, with emission peaks at 473 nm and 501 nm.

9. Synthesis of di(μ-hpp)bis[(dipyridylamino)platinum(II)]=Compound 6

Compound 6

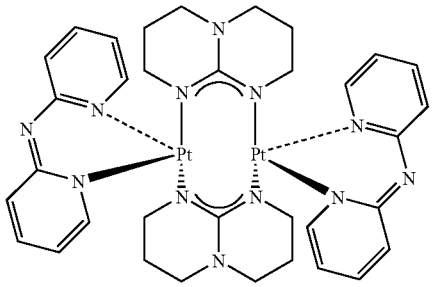

1.25 mmol (1 g) di(μ-chloro)bis[(dipyridylamino)platinum(II)] (compound 3) are suspended in 10 mL dichloromethane and chilled to −70° C. A mixture of 2.496 mmol (134.8 mg) sodium methylate and 2.496 mmol (347.4 mg) Hhpp suspended in 35 mL dichloromethane and likewise chilled to −70° C. is added to the above mixture. The reaction mixture turns yellow. It is left to react for 48 h at room temperature, while stirring. Then the substance is filtered through the P4 frit and washed several times with dichloromethane. The filtrate is concentrated and vacuum dried.

Yield: 1.04 g (83%).

Figure 2C:
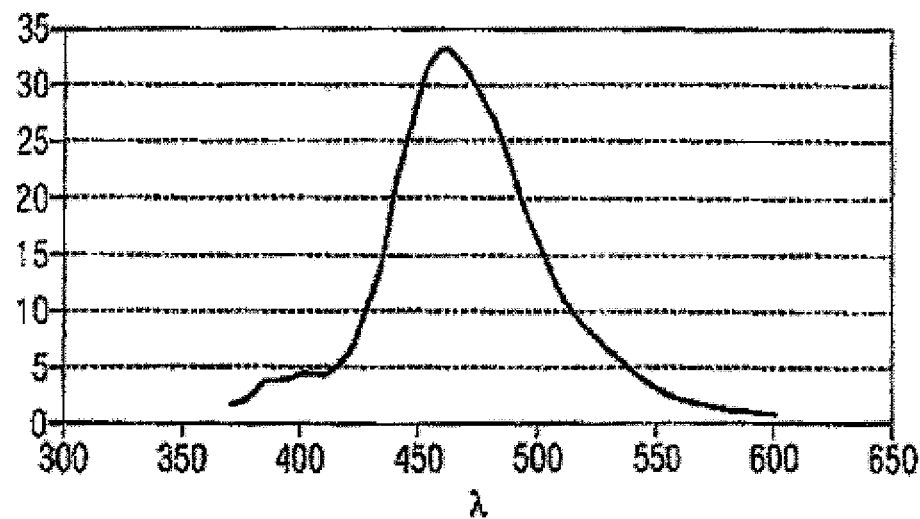

FIG. 2c shows the photoluminescence spectrum of Compound 6, with emission peak at 463 nm.

The scope of protection of the invention is not limited to the examples given hereinabove. The invention is embodied in each novel characteristic and each combination of characteristics, which includes every combination of any features which are stated in the claims, even if this feature or combination of features is not explicitly stated in the examples.

The invention claimed is:

1. A radiation-emitting organic component comprising a substrate, at least one lower electrode layer, at least one organic radiation-emitting layer and an upper electrode layer arranged thereon, wherein the radiation-emitting layer has a matrix, the matrix containing at least one radiation-emitting metal complex, wherein the metal complex comprises at least one metal central atom M selected from a group consisting of Ir, Pt, Au, Re, Ru, Os, Pd and lanthanoids, wherein the metal complex has at least one substituted or unsubstituted guanidinate ligand, with a guanidine anion group, wherein the guanidine anion group is doubly coordinated to the central atom present in the metal complex or bridging the at least one metal central atom M and another metal atom in an at least dinuclear metal complex, wherein the guanidine anion group comprises the following structural unit:

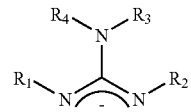

$R_1$, $R_2$, $R_3$ and $R_4$ can independently be H, unbranched, branched, condensed and cyclic alkyl residues, alkylene residues, substituted or unsubstituted aromatic compounds, condensed aromatic compounds, substituted or unsubstituted heterocycles and condensed heterocycles as well as completely or partially substituted alkyl residues, aromatic compounds, condensed aromatic compounds, heterocycles and condensed heterocycles, and/or wherein $R_1$ and $R_4$ and/or groups $R_2$ and $R_3$ and/or $R_3$ and $R_4$ are bonded to each other and/or wherein the alkyl residues and alkylene residues comprise at least one substituent selected from the group consisting of ether groups, ester, amide, and carbonate groups.

2. The component according to claim 1, wherein the component has one or more auxiliary layers in addition to the radiation-emitting layer between the electrode layers in each case.

3. The component according to claim 1, wherein the substrate and the lower electrode layer are transparent.

4. The component according to one of claims 1, wherein the metal complex contained in the radiation-emitting layer has at least one hpp ligand as guanidinate ligand.

5. The component according to claim 1, wherein the guanidinate ligand is bicyclic and the bicyclic system contains the N atoms of the guanidine anion group.

6. The component according to claim 1, wherein the metal complex contained in the emission layer is homoleptic.

7. The component according to claim 1 that emits deep blue, light blue and/or blue-green.

* * * * *